(12) United States Patent
Hyler et al.

(10) Patent No.: US 11,723,995 B2
(45) Date of Patent: Aug. 15, 2023

(54) STERILIZING MATS AND METHODS OF USING THE SAME

(71) Applicants: Mary-Allison Hyler, Marina del Rey, CA (US); Adam K. Fontecchio, Downingtown, PA (US)

(72) Inventors: Mary-Allison Hyler, Marina del Rey, CA (US); Adam K. Fontecchio, Downingtown, PA (US)

(73) Assignees: Mary-Allison Hyler, Marina del Rey, CA (US); Adam K. Fontecchio, Downingtown, PA (US)

( * ) Notice: Subject to any disclaimer, the term of this patent is extended or adjusted under 35 U.S.C. 154(b) by 262 days.

(21) Appl. No.: 17/186,469

(22) Filed: Feb. 26, 2021

(65) Prior Publication Data

US 2021/0268134 A1   Sep. 2, 2021

Related U.S. Application Data

(60) Provisional application No. 62/983,066, filed on Feb. 28, 2020.

(51) Int. Cl.
*A61L 2/10* (2006.01)
*A61L 2/26* (2006.01)
*G02B 6/42* (2006.01)

(52) U.S. Cl.
CPC .................. *A61L 2/10* (2013.01); *A61L 2/26* (2013.01); *G02B 6/4202* (2013.01); *A61L 2202/11* (2013.01)

(58) Field of Classification Search
CPC ............ A61L 2/10; A61L 2/26; G02B 6/4202
See application file for complete search history.

(56) References Cited

U.S. PATENT DOCUMENTS

| 7,875,869 | B1 | 1/2011 | Shadan | |
| 9,339,571 | B2* | 5/2016 | Bilenko | A61L 2/10 |
| 2009/0117001 | A1 | 5/2009 | Hyde et al. | |
| 2011/0291995 | A1 | 12/2011 | Shr et al. | |
| 2013/0048876 | A1* | 2/2013 | Crawford | A61L 2/10 |
| | | | | 250/492.1 |
| 2013/0259742 | A1* | 10/2013 | Kerr | A61L 2/10 |
| | | | | 250/431 |
| 2018/0132697 | A1 | 5/2018 | Desu-Kalyanam | |
| 2018/0236113 | A1 | 8/2018 | Gross et al. | |

* cited by examiner

*Primary Examiner* — Eliza W Osenbaugh-Stewart
(74) *Attorney, Agent, or Firm* — Flaster Greenberg P.C.

(57) ABSTRACT

Sterilizing devices, preferably foot mats, comprise: a support member having an arrangement structure and a plurality of UV light emitting members, where the support member is configured for total internal reflection of UV light from the UV light emitting members; a power source providing power to the plurality of UV light emitting members; and a translucent substrate having an upper surface and a lower surface; wherein the translucent substrate is disposed above the support member such that the lower surface of the translucent substrate can be brought into contact with an upper region of the support member when a downward force is applied to the upper surface of the translucent substrate; and wherein the contact between the lower surface of the translucent substrate and the support member breaks the total internal reflection in the area of contact such that UV light is emitted through the translucent substrate.

20 Claims, 5 Drawing Sheets

STERILIZING MATS AND METHODS OF USING THE SAME

CROSS-REFERENCE TO RELATED APPLICATIONS

This application claims the benefit of U.S. Provisional Patent Application No. 62/983,066, filed Feb. 28, 2020, the entire contents of which are hereby incorporated herein by reference.

BACKGROUND OF THE INVENTION

Bacteria, viruses, germs, molds, fungi and other undesirable, pathogenic microorganisms are transferred from one area to another through contact with people, animals and objects that come into contact with them.

The soles of people's footwear are a primary vehicle for pathogens entering homes, healthcare facilities and other buildings. Similarly, bare feet can be exposed to microorganism contamination when walking bare foot outside or in locker rooms, pools, showers and the like and further spread them. The pathogens can cause sickness, disease, and possible death. The soles of people's footwear and the outer surfaces of other objects such as suitcases, handbags, purses, briefcases, packages, and the like which come into contact with contaminated areas as airport bathrooms, bars, schools, hospitals and restaurants which may expose them to domestic and international microorganisms also become contaminated and thereby become a source of further microbial contamination and spreading. Thus, footwear and other objects can carry microorganisms into the home, office, healthcare facility, and other personal and public areas, and to those most susceptible to microorganism exposure, such as young children, the elderly, and the immunocompromised.

Further, house pets that have come into contact with contaminated areas such as parks, yards, and the like can also carry undesirable microorganisms into the home. In livestock areas cattle, horses, sheep and the like constantly come into contact with undesirable microorganisms and spread them around on the paws, hooves or feet. It is therefore desirable to eliminate or significantly reduce the amounts of these microorganisms from surfaces that carry them.

Door mats, the primary means for cleaning shoe bottoms, remove dirt but not pathogens, and can quickly become an incubator for germs. Disposable booties or shoe covers are used in professional environments, but do not work well in public areas, as people tend to be self-conscience about wearing them, and there are safety concerns over people tripping while wearing such covers.

Other solutions such as liquid dips are not practical for high traffic areas and require frequent maintenance to stay effective and can create other problems such as slippery soles, tracking of the fluids and potential exposure to toxic materials relating to the disinfectant.

Other technologies used to sanitize footwear can include devices that incorporate light bulbs that emit short-wavelength ultraviolet ("UV-C") light directed at the bottom of footwear to destroy pathogens that may be associated therewith. These devices, however, are typically bulky due to the large size of the UV-C light bulbs, they may be ineffective at preventing or limiting unintended exposure to the UV-C light, they can be costly due to sensors and construction, and are oftentimes difficult to operate.

Thus, more efficient devices and methods and more suitable materials are needed to properly eliminate or significantly reduce undesirable microorganisms.

BRIEF SUMMARY OF THE INVENTION

Embodiments of the present invention are directed, in general, to sterilizing devices and methods of using such devices. More particularly, various embodiments of the present invention thus provide sterilizing devices, preferably in the form of floor mats, which emit ultraviolet light incident upon the bottoms of feet and shoes. In the various embodiments of the present invention, ultraviolet light emission is activated upon a downward pressure applied to an upper surface of the device. Additionally, in various embodiments of the present invention, ultraviolet light emission is terminated upon removal of the downward pressure applied to the upper surface of the device.

One embodiment of the present invention includes a sterilizing device comprising: a support member comprising an arrangement structure and a plurality of UV light emitting members, wherein the support member is configured for total internal reflection of UV light from the UV light emitting members; a power source providing power to the plurality of UV light emitting members; and a translucent substrate having an upper surface and a lower surface; wherein the translucent substrate is disposed above the support member such that the lower surface of the translucent substrate can be brought into contact with an upper region of the support member when a downward force is applied to the upper surface of the translucent substrate; and wherein the contact between the lower surface of the translucent substrate and the support member breaks the total internal reflection in the area of contact such that UV light is emitted through the translucent substrate. Another embodiment of the present invention includes a method, the method comprising: providing a sterilizing device in accordance with any of the various device embodiments of the present invention; placing the powered device in a path of foot traffic; and permitting the device to be tread upon and activated.

In various preferred embodiments of the present invention, the arrangement structure comprises a mesh screen and the plurality of UV light emitting members comprises two or more optical fibers connected to an illuminator, wherein the illuminator is connected to the power source, wherein each optical fiber has a longitudinal axis, and wherein the mesh is sized to support the two or more optical fibers such that the two or more optical fibers are arranged with their longitudinal axes substantially parallel to one another and an end of each optical fiber not connected to the illuminator is proximate to a lower surface of the translucent substrate.

In other various preferred embodiments of the present invention, the arrangement structure comprises a housing having two or more compartments and the plurality of UV light emitting members comprises two or more UV light sources connected to the power source, wherein each compartment contains at least one of the two or more UV light sources, and wherein each compartment has an upper region configured to provide total internal reflection within the compartment.

Other aspects, features and advantages will be apparent from the following disclosure, including the detailed description, preferred embodiments, and the appended claims.

BRIEF DESCRIPTION OF SEVERAL VIEWS OF THE DRAWINGS

The foregoing summary, as well as the following detailed description of preferred embodiments of the invention, will be better understood when read in conjunction with the appended drawings. For purposes of illustration the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
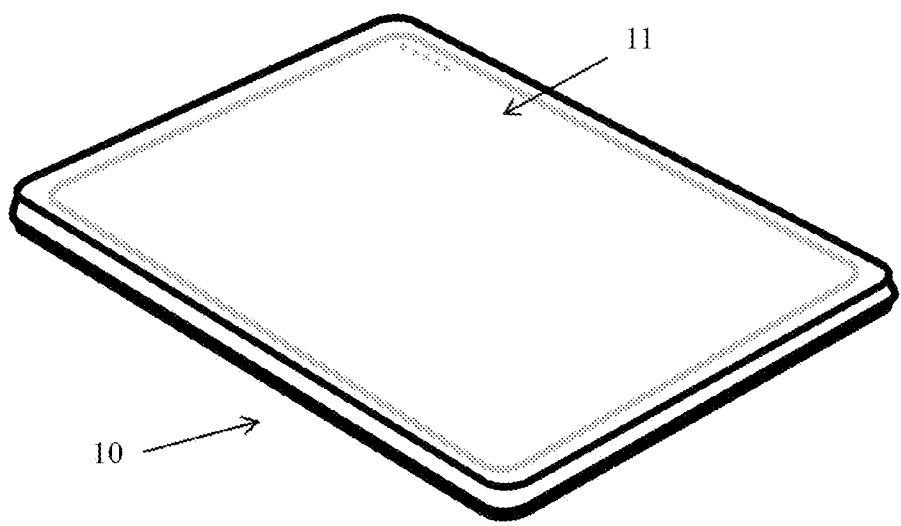
FIG. 1 is a diagrammatical view of the exterior of a sterilizing device in accordance with one embodiment of the present invention.

As used herein, the singular terms "a" and "the" are synonymous and used interchangeably with "one or more" and "at least one," unless the language and/or context clearly indicates otherwise. Accordingly, for example, reference to "a member" or "the member" herein or in the appended claims can refer to a single member or more than one member. Additionally, all numerical values, unless otherwise specifically noted, are understood to be modified by the word "about."

For simplicity and clarity of illustration, elements in the figures are not necessarily to scale, and the same reference numbers in different figures denote the same elements. For clarity of the drawing, various elements are illustrated as having generally straight line edges and precise angular corners. However, those skilled in the art understand that the edges need not be straight lines and the corners need not be precise angles.

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the object described and designated parts thereof. The terminology includes the words above specifically mentioned, derivatives thereof and words of similar import.

Figure 2:
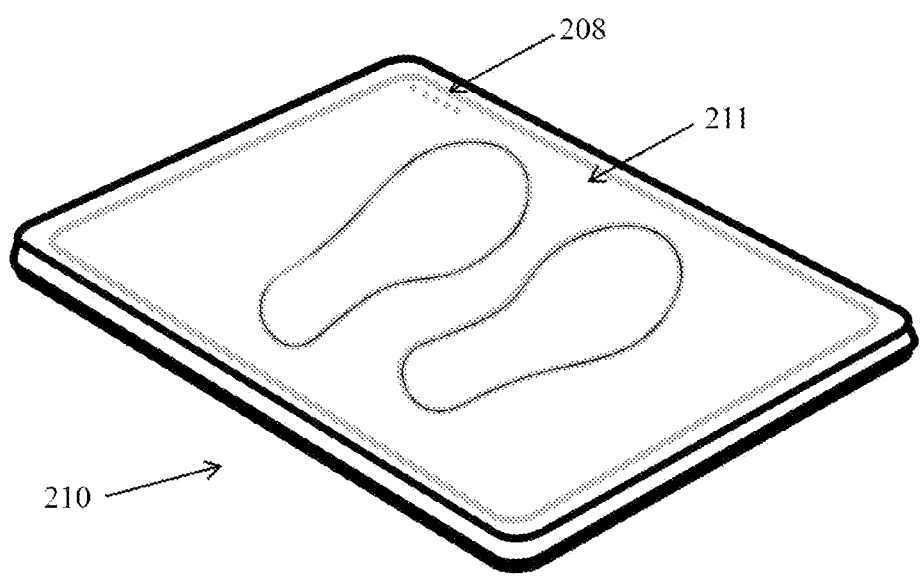
FIG. 2 is a diagrammatical view of the exterior of a sterilizing device in accordance with another embodiment of the present invention.

Sterilizing devices in accordance with the various embodiments of the present invention emit UV light which is incident upon the bottoms of shoes and feet when a downward pressure is applied to the upper surface of the device. Sterilizing devices in accordance with the various embodiments of the present invention can be placed on the ground, such as like a door mat, or they can also be embedded within a floor and can be surrounded by flooring material. For example, referring to FIG. 1, a "door mat" style sterilizing device 10 in accordance with an embodiment of the present invention is depicted. A translucent substrate 11 serves as the upper surface of the device. In various embodiments of the present invention, the upper surface may comprise a decorative translucent substrate. For example, referring to FIG. 2, a "door mat" style sterilizing device 210 in accordance with an embodiment of the present invention is depicted having a translucent substrate 211 which include decorative markings 215, which may include colorings, patterns, insignia, labels, words, shapes, etc. For example, in the embodiment shown in FIG. 2, a decorative marking can include foot print shapes. In various embodiments, for example, decorative markings can include wood grains or ceramic colorings and patterns. Additionally, in various embodiments, the upper surface may be texturized for user stability.

Sterilizing devices in accordance with the various embodiments of the present invention include a support member below a translucent substrate. Support members suitable for use in accordance with the various embodiments of the present invention comprise an arrangement structure and a plurality of UV light emitting members. As used herein, "plurality" means more than one. Preferably, the plurality of UV light emitting members is an array of several such UV light emitting members. A support member in accordance with various embodiments of the present invention may be directly below and support the translucent substrate, or it may be housed within a frame which supports the translucent substrate. In other words, in various embodiments, a support member may comprise an arrangement structure which holds a plurality of UV light emitting members and also supports the translucent substrate above it, for example with members extending upwards and providing underlying contact with the lower surface edges of a translucent substrate. In other various embodiments, for example, a support member may comprise an arrangement structure which holds a plurality of UV light emitting members and the entire arrangement structure and plurality of UV light emitting members are disposed in a frame member, the frame providing underlying support to the lower surface edges of the translucent substrate. In such various embodiments, the frame member may have a floor and walls, or may be walls with no floor, or may be walls with supporting cross members in place of a floor, and may have any perimeter shape, for example, rectangular, so long as the frame member accommodate the arrangement structure and plurality of UV light emitting members.

In accordance with various embodiments of the present invention, an arrangement structure can comprise any rigid member capable of holding a plurality of UV light emitting members in a specified arrangement. Thus, for example, an arrangement structure can include a mesh screen having openings sufficiently sized to accommodate, for example, optical fibers. In various embodiments of the present invention, a mesh screen with regularly repeating openings sized to accommodate short optical fibers can be used as the arrangement structure. The mesh screen may be comprised of various materials, such as plastic, metals and composites. In various preferred embodiments, a mesh screen suitable for use as an arrangement structure can comprise one or more recycled metals.

Mesh screens suitable for use as an arrangement structure in various embodiments of the invention can preferably have a thickness (the dimension perpendicular to the plane of the mesh screen) of at least about 1% of the length of the optical fibers held in place by the mesh screen, and up to almost 100% of the optical fiber length, so long as some minimal portion of an upper end of each optical fiber protrudes (i.e., sticks out) from the mesh screen and is capable of being contacted by a lower surface of the translucent substrate. In various preferred embodiments, the thickness of a mesh screen suitable for use as an arrangement structure is from 1 to 50% of the length of the optical fibers held in place by the screen, and more preferably 10 to 25%. The regularly repeating openings of a mesh screen suitable for use as an arrangement structure in accordance with various embodiments of the present invention can be of any shape which can accommodate optical fibers. For example, the openings can be circular or any polygonal shape such as parallelograms or hexagonal, etc. Preferably, the openings are sized to fit the cross-sectional dimensions of the optical fibers so as to limit their lateral movement. In accordance with various preferred embodiments, the openings in the mesh screen are circular and coincide with the shape and outer dimension size of the optical fibers to provide a snug fit and limit lateral movement of the fibers.

A mesh screen suitable for use as an arrangement structure in accordance with various embodiments of the present invention can also further comprise a lower tray, which may be integrally connected to the mesh screen to provide further support for the lower ends of the optical fibers. For example, a lower tray may be spaced apart from the mesh screen by vertical support members which connect the mesh screen to the tray. Such vertical support members may be located along the outer edges of the mesh screen and the tray, or may be located at interior locations, or both. In some embodiments, a lower tray can be connected to the mesh screen by one or more vertical walls, which may also be integral to the screen and tray.

In such embodiments which include a lower tray, the tray may be configured so that the fiber ends pass through the tray for connection to an illuminator, or the tray may be configured such that it provides light transmissive connection to the ends of the fibers. For example, a lower tray may hold or may comprise a waveguide, to which lower ends of the optical fibers are connected for light transmission. The illuminator (i.e. source of UV light) is then connected to the waveguide at a peripheral point. Methods and processes for connecting optical fibers to a waveguide are known and any such method or process which provides for light transmission from waveguide to fiber can be used. Connecting optical fibers to waveguides and other sources of illumination are described in: Hecht, E., *Optics, 5th* Ed., Pearson Educ., 2017; Saleh, B., et al., *Fundamentals of Photonics, 2nd* Ed., Wiley, 2007; and Crisp. J., et al., *Introduction to Fiber Optics, 3rd* Ed., Elsevier Ltd., 2005; the entire contents of each of which are hereby incorporated herein by reference. Preferably, various methods of connecting optical fibers to waveguides or any other source of illumination which are known to minimize loss and increase transmission may be employed but are not necessary. On the other hand, in various embodiments, the optical fibers can be routed through the lower tray and out one or more sides of the device, or simply directly out one or more sides of the device (without being routed through the lower tray), and connected to the illuminator at a peripheral area of the device.

As discussed above, in various embodiments according to the present invention, the plurality of UV light emitting members can be a plurality of optical fibers. In the various embodiments according to the present invention where the plurality of UV emitting light sources include optical fibers, the arrangement structure preferably holds the plurality of optical fibers with their longitudinal axes parallel to one another. UV light suitable for use in the various embodiments of the present invention can preferably include light in the UV-C wavelength range. UV-C generally refers to light with wavelengths of from 100 nm to 280 nm. In various embodiments, including those in which UV-C light is emitted, optical fibers can comprise hollow core optical fibers. In various embodiments according to the present invention, the UV light emitting members can comprise one or more LEDs, bulbs, lasers, laser diodes or natural light sources. In various embodiments, the UV light emitting members can comprise a light collection structure, such as a light tube, that collects sunlight and funnels it to a waveguide or other light distribution device for illuminating the optical fibers. Thus, an illuminator providing UV light to optical fibers and/or light pipes, directly or indirectly can comprises any of the aforementioned LEDs, bulbs, lasers, laser diodes and sunlight.

Figure 3A:
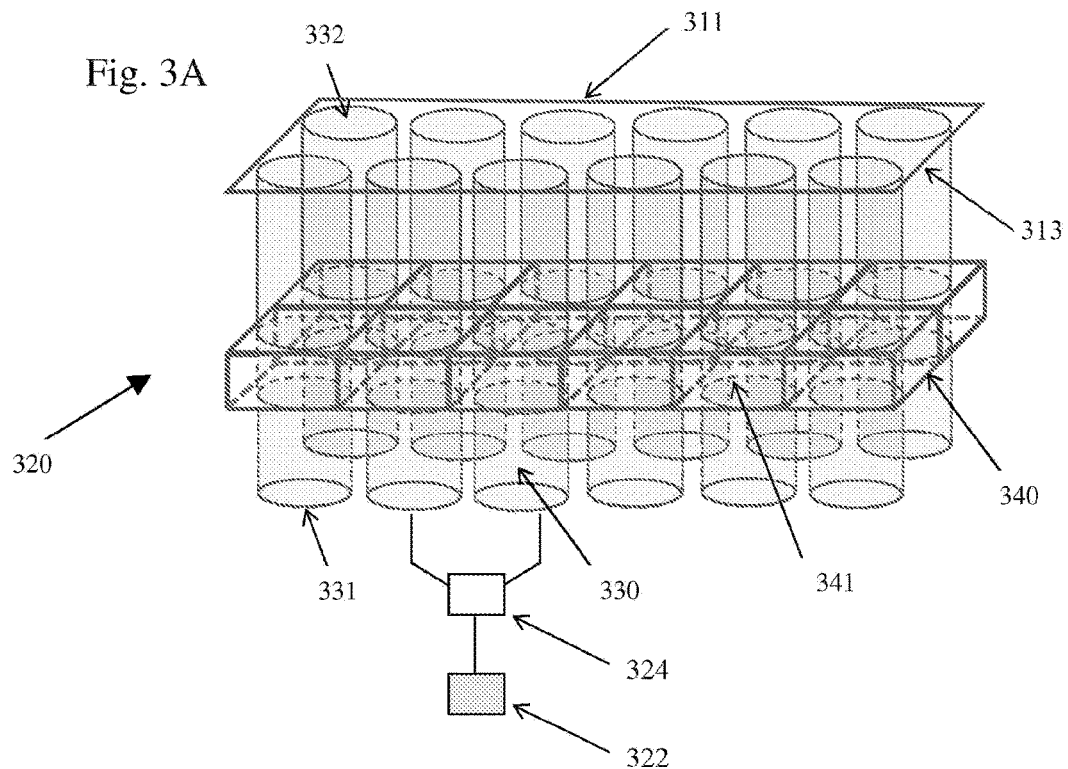
FIG. 3A is a perspective view of a portion of an arrangement structure and a portion of a plurality of UV light emitting members in accordance with an embodiment of the present invention.
Figure 3B:
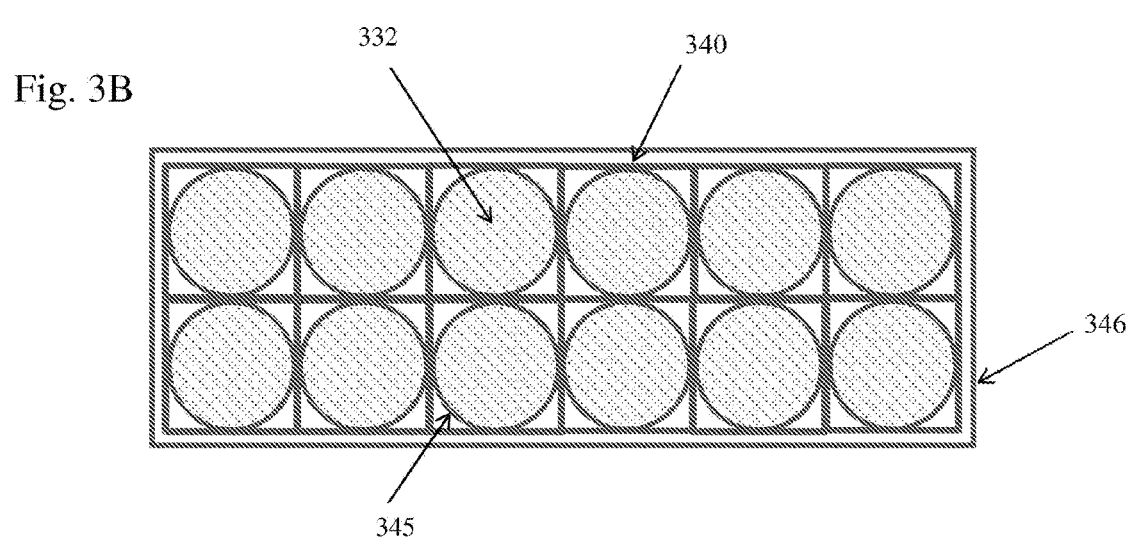
FIG. 3B is a top plan view of the portion of the arrangement structure and the plurality of UV light emitting members depicted in FIG. 3A.
Figure 4A:
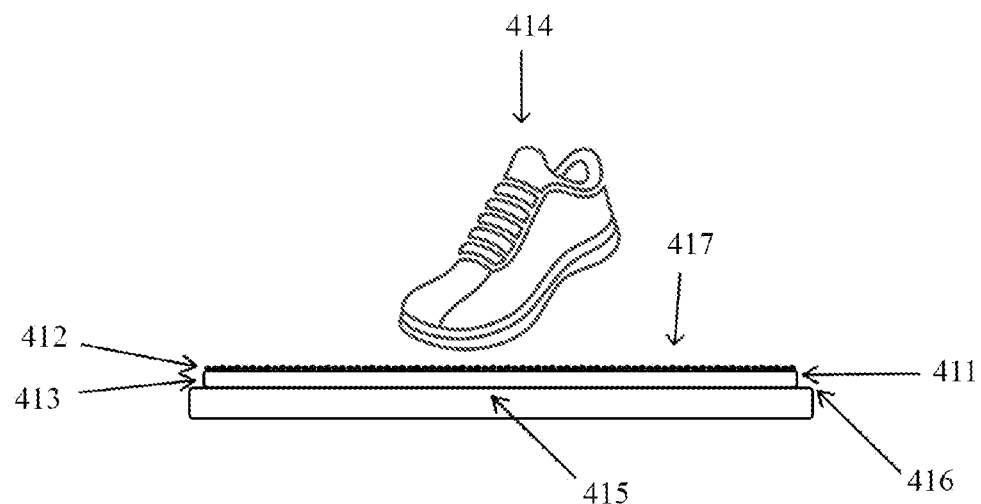
FIG. 4A is a cross-section view of an embodiment of the present invention showing a perimeter portion having an abrasive surface.
Figure 4B:
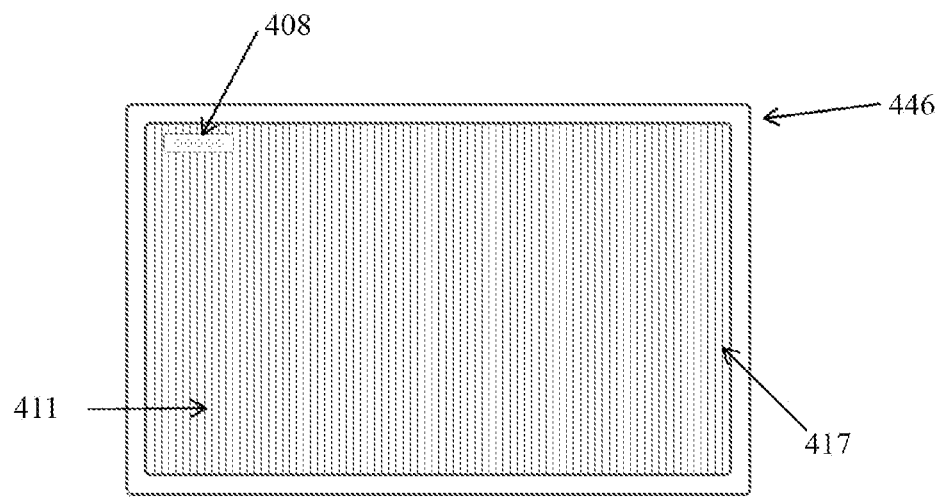
FIG. 4B is a top-down view of embodiment of the present invention showing an abrasive surface.
Figure 5A:
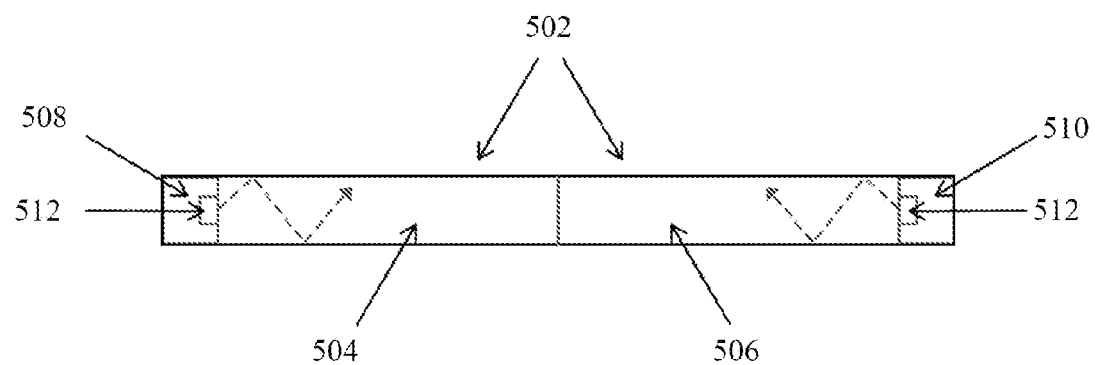
FIG. 5A is a cross-section view of a portion of an embodiment of the present invention showing the arrangement structure comprising a housing.
Figure 5B:
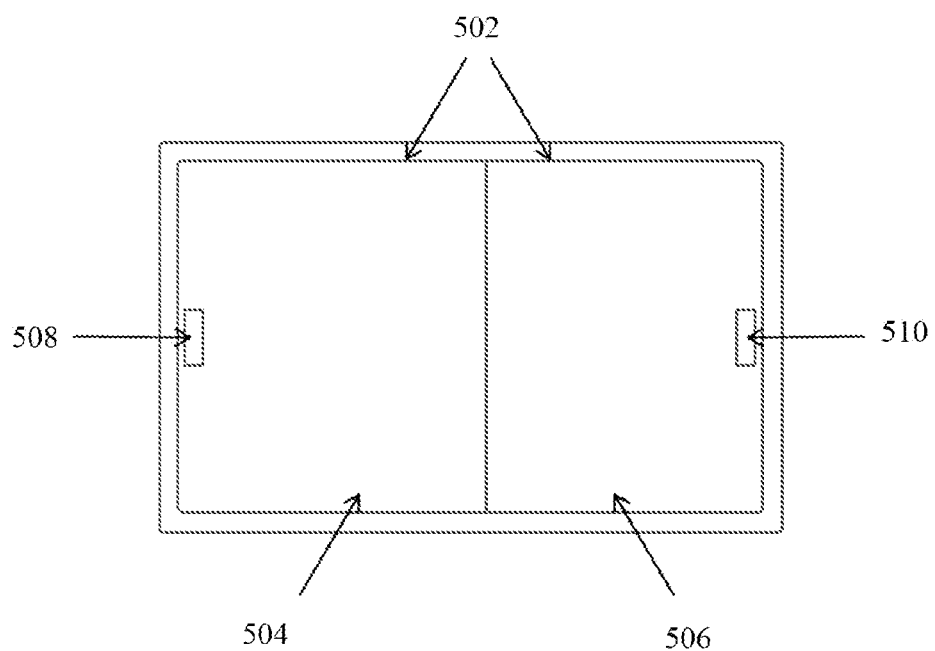
FIG. 5B is a top-down view of the portion of the embodiment of the present invention showing the arrangement structure comprising a housing.
Figure 6A:
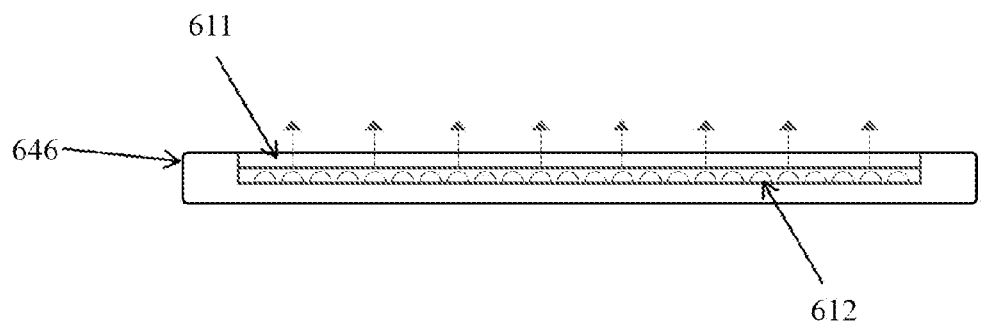
FIG. 6A is a cross-section view of an embodiment of the present invention showing an arrangement structure comprising UV-emitting LEDs.
Figure 6B:
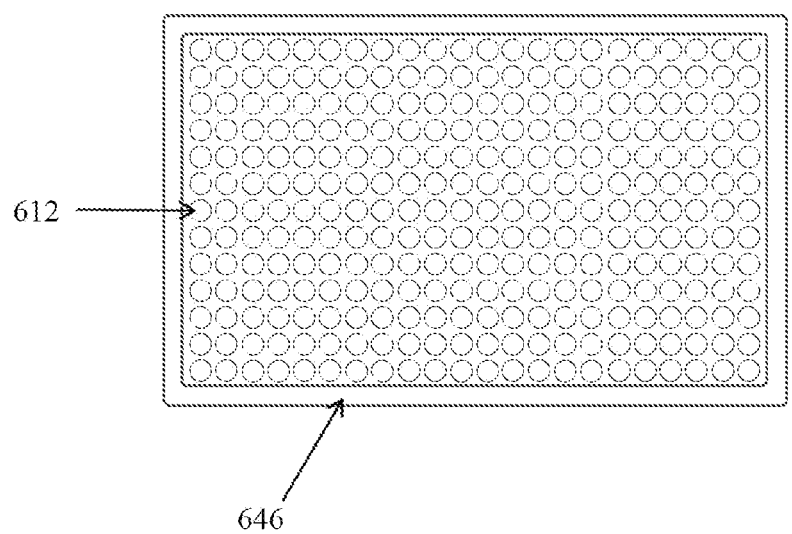
FIG. 6B is a top-down view of an embodiment of the present invention showing the arrangement structure comprising UV-emitting LEDs.

Referring to FIGS. 3A and 3B, views of a portion of an arrangement structure and a portion of a plurality of UV light emitting members in accordance with an embodiment of the present invention are shown. Referring to FIG. 3A, specifically, a perspective view of a portion of a support member 320 in accordance with one embodiment of the present invention is depicted. A mesh screen 340 having a thickness (in the direction perpendicular to the plane of the mesh screen) 341, further has repeating openings through which optical fibers 330 run. In the embodiment depicted in FIGS. 3A and 3B, the fibers have a round cross-sectional shape and the repeating openings in the mesh screen are circular and sized to the outer diameter of the optical fibers. A bottom end of the optical fibers 331 can be connected to a waveguide or other source of illumination (not shown). An upper end 332 of the optical fibers can be shaped (not shown) to provide for total internal reflection within each fiber. For example, the upper end 332 of each fiber can be shaped to be a hemispheric dome having a radius that is one half of the outer diameter of the optical fiber.

Referring to FIG. 3B, each repeating opening 345 of mesh screen 340 having a thickness 341 is shaped and sized to snugly accommodate the optical fibers. The optical fibers are 10 arranged and held in place such that they are aligned with their longitudinal axes parallel to one another and perpendicular to the plane of the mesh screen, so that in a plan view as shown, the upper surface 332 of each fiber is visible.

In various embodiments according to the present invention, an arrangement structure can comprise a housing having two or more compartments, preferably an array of compartments, each compartment containing at least one or more UV light source. For example, a housing may comprise a top, a bottom and sides, wherein the volume of the housing is segmented into an array of individual, interconnected, cells, each cell having sides that define the cell, wherein the sides of the cells comprise structural material and are positioned orthogonal to the bottom of the housing and extend from the bottom of the housing fully or partially to the top of the housing, each cell comprising a UV light emitting source positioned in the bottom of the cell, wherein each cell has an upper region (including at least the top of the cell) that is configured (i.e., shaped or designed) to provide total internal reflection ("TIR") within the cell.

In the various embodiments of the present invention, a support member is configured for total internal reflection of UV light from the UV light emitting members. Accordingly, for example, in embodiments wherein the plurality of UV light emitting members comprise optical fibers, the upper ends (the ends proximate to the translucent substrate) of the optical fibers can be shaped to provide TIR. In other embodiments, for example where the arrangement structure comprises a housing having a plurality of separate compartments, the housing compartments may have an upper region that is shaped or contoured to provide TIR within each compartment. Shapes and contours which provide TIR (for example, a hemispheric dome shape), and methods for shaping optical fibers for TIR, are known and described, for example in various texts including: Hecht, E., *Optics, 5th* Ed., Pearson Educ., 2017, and Saleh, B., et al., *Fundamentals of Photonics, 2nd* Ed., Wiley, 2007; the entire contents of each of which are hereby incorporated herein by reference.

Suitable power sources which can be used in the sterilizing devices according to the various embodiments of the present invention can include hard wired AC electricity, one or more batteries, solar cells, fuel cells and other portable power sources. In various embodiments, multiple power sources can be utilized with a switching mechanism, for example, to alternate between a hard-wired AC power source and a portable or rechargeable power source.

A translucent substrate having an upper surface and a lower surface can comprise any material which is partially or completely translucent to UV light. For example, in various embodiments, a translucent substrate can comprise a material such as quartz, UV fused silica, barium fluoride, an optical borosilicate crown glass, such as BK7 glass which is commercially available from a number of sources, or the like. In various embodiments, a translucent substrate can comprise, for example, a UV translucent polymer such as cyclic olefin copolymers. A translucent substrate in accordance with various embodiments can have any thickness so long as it is not so thick that at least some UV light is capable of being transmitted through the substrate and so long as it is not so thin that the weight of an average user (e.g., human, dog, etc.) does not destroy its structural integrity. Generally, a translucent substrate in accordance with various embodiments of the present invention will be sized to be coextensive in area with the support member, but can be larger or smaller. As discussed above, a translucent substrate in accordance with various embodiments of the invention may include decorative markings.

A translucent substrate suitable for use in accordance with various embodiments of the present invention, may be translucent or even opaque with perforations or holes to allow for transmission of UV light.

In certain embodiments, such as for example, sterilizing devices for use in locker rooms, swimming pool areas and the like, a translucent substrate can be omitted as a bare animal or human foot, particularly in instances where the sole of the foot is wet, can be suitable for breaking TIR of a support member. In other words, direct contact of the bare foot with the upper ends of optical fibers can break TIR within the fibers at the upper ends.

In the various embodiments of sterilizing devices according to the present invention, the translucent substrate is disposed above the support member such that the lower surface of the translucent substrate can be brought into contact with an upper region of the support member, which may for example comprise the top ends of optical fibers or upper surfaces of a housing compartment, when a downward force is applied to the upper surface of the translucent substrate. The downward force is supplied by the weight of an individual or object on the translucent substrate. Accordingly, the distance between the lower surface of the translucent substrate and the upper ends of the optical fibers or upper region of the support member is minimized based on the flexural strength of the substrate material and its thickness such that the small amounts of weight (e.g., a child, a roller suitcase, a pet) will cause deformation of the translucent substrate such that the lower surface thereof comes into contact with the upper ends of the optical fibers or the upper region of the support member. Thus, for example, in embodiments employing UV fused silica glass having a thickness of 10 mm, the lower surface of the UV fused silica glass can be positioned 1 to 5 mm from the upper ends of the optical fibers so that a weight of 50 kg causes the lower surface to come into contact with the upper ends of the optical fibers.

In accordance with various embodiments of sterilizing devices of the invention, a downward pressure on the translucent substrate causes contact between the lower surface of the translucent substrate and the support member such that the total internal reflection in the area of contact is broken and UV light is emitted through the translucent substrate. Breaking of total internal reflection in this manner is described in Hecht and Saleh, incorporated by reference above. Any amount of contact is sufficient to allow light to pass through the area of contact, however, in various embodiments, UV light emission can be maximized by shaping the lower surface of the translucent substrate to provide a larger area of contact. For example, optical fibers having hemispheric dome upper ends can be used and the lower surface of the translucent substrate can be provided with indentations corresponding to the hemispheric domes. In such embodiments, light would be emitted in all directions where there is contact between the hemispheric dome and the corresponding indentation. Furthermore, in various embodiments, the translucent substrate can be segmented such that material gaps allow for reflection of the emitted light entirely in an upward direction.

In various embodiments, a sterilizing device may include a visual, auditory or vibrational indicator signaling one or more criterion is met. For example, in various embodiments, additional light sources, including wavelengths in the visible spectrum can be added such that an indication of operation visible to the user can be seen. In various embodiments, an auditory indicator can signal the passage of a certain period of time of operation.

In various embodiments, sterilizing devices can be provided as a kit comprising: a support member having an arrangement structure and a plurality of UV light emitting members, wherein the support member is configured for total internal reflection of UV light from the UV light emitting members; a power source configured to provide power to the plurality of UV light emitting members or a connection member configured to be connected to a power source; and a translucent substrate having an upper surface and a lower surface; with instructions for assembly and installation.

It will be appreciated by those skilled in the art that changes could be made to the embodiments described above without departing from the broad inventive concept thereof.

It is understood, therefore, that this invention is not limited to the particular embodiments disclosed, but it is intended to cover modifications within the spirit and scope of the present invention as defined by the appended claims.

What is claimed is:

1. A sterilizing device comprising:
   a support member comprising an arrangement structure and a plurality of UV light emitting members, wherein the support member is configured for total internal reflection of UV light from the UV light emitting members;
   a power source configured to provide power to the plurality of UV light emitting members; and
   a translucent substrate having an upper surface and a lower surface;
   wherein the translucent substrate is disposed above the support member such that the lower surface of the translucent substrate can be brought into contact with an upper region of the support member when a downward force is applied to the upper surface of the translucent substrate; and wherein the contact between the lower surface of the translucent substrate and the support member is configured to break the total internal reflection in the area of contact such that UV light is emitted through the translucent substrate.

2. The sterilizing device according to claim 1, wherein the arrangement structure comprises a mesh screen and the plurality of UV light emitting members comprises two or more optical fibers connected to an illuminator, wherein the illuminator is connected to the power source, wherein each optical fiber has a longitudinal axis, and wherein the mesh is sized to support the two or more optical fibers such that the two or more optical fibers are arranged with their longitudinal axes substantially parallel to one another.

3. The sterilizing device according to claim 2, wherein the longitudinal axes of the two or more optical fibers are arranged substantially normal to the lower surface of the translucent substrate, and wherein an end of each of the two or more optical fibers which is proximate to the lower surface of the translucent substrate is shaped to provide total internal reflection within the optical fiber.

4. The sterilizing device according to claim 3, wherein at least one of the two or more optical fibers comprises a hollow core optical fiber.

5. The sterilizing device according to claim 4, wherein the illuminator provides light to the two or more optical fibers in the UV-C spectrum.

6. The sterilizing device according to claim 5, wherein the translucent substrate comprises tempered glass.

7. The sterilizing device according to claim 5, wherein the translucent substrate is decorative.

8. The sterilizing device according to claim 5, further comprising a frame in which the support member is disposed.

9. The sterilizing device according to claim 1, wherein the translucent substrate is decorative.

10. The sterilizing device according to claim 1, further comprising a frame in which the support member is disposed.

11. The sterilizing device according to claim 1, wherein the arrangement structure comprises a housing having two or more compartments and the plurality of UV light emitting members comprises two or more UV light sources connected to the power source, wherein each compartment contains at least one of the two or more UV light sources, and wherein each compartment has an upper region configured to provide total internal reflection within the compartment.

12. The sterilizing device according to claim 11, wherein each of the two or more compartments has a sidewall extending in a direction normal to the translucent substrate, and wherein each of the two or more compartments has the same cross-sectional shape parallel to the translucent substrate.

13. The sterilizing device according to claim 12, wherein each of the two or more compartments has a circular cross-sectional shape.

14. The sterilizing device according to claim 12, wherein each of the two or more compartments has three or more sidewalls, and wherein each of the two or more compartments shares a sidewall with at least one neighboring compartment.

15. The sterilizing device according to claim 12, wherein each of the two or more compartments has a hexagonal cross-sectional shape, and wherein at least one of the two or more UV light sources comprises a UV-emitting LED.

16. The sterilizing device according to claim 11, wherein at least one of the two or more UV light sources comprises a UV-emitting LED.

17. The sterilizing device according to claim 11, wherein the two or more UV light sources emit light in the UV-C spectrum.

18. The sterilizing device according to claim 11, wherein the translucent substrate comprises tempered glass.

19. The sterilizing device according to claim 1, further comprising a perimeter portion disposed proximate to at least one edge of the translucent substrate, the perimeter portion having an abrasive surface.

20. The sterilizing device according to claim 1, further comprising a visual indicator signaling one or more criterion is met.

* * * * *